United States Patent
Keller

(10) Patent No.: US 6,443,612 B1
(45) Date of Patent: Sep. 3, 2002

(54) DYNAMIC MIXER

(76) Inventor: Wilhelm A. Keller, Obstgartenweg 9, CH-6402 Merlischachen (CH)

( * ) Notice: Subject to any disclaimer, the term of this patent is extended or adjusted under 35 U.S.C. 154(b) by 0 days.

(21) Appl. No.: 09/716,323

(22) Filed: Nov. 21, 2000

(30) Foreign Application Priority Data

Dec. 2, 1999 (CH) .................................... 1999 2210/99
Mar. 18, 2000 (EP) ........................................... 00810432

(51) Int. Cl.⁷ ................................................. B01F 7/00
(52) U.S. Cl. .................. 366/307; 366/329.1; 222/145.6
(58) Field of Search ........................ 366/172.1, 172.2, 366/176.1, 181.5, 307, 316, 328.2, 328.3, 329.2, 329.1; 222/145.5, 145.6

(56) References Cited

U.S. PATENT DOCUMENTS

| | | | |
|---|---|---|---|
| 3,051,455 A | * | 8/1962 | Magester |
| 3,226,093 A | * | 12/1965 | Gugel et al. |
| 3,302,832 A | * | 2/1967 | Hardman et al. |
| 3,390,814 A | * | 7/1968 | Creighton, Jr. et al. |
| 3,570,719 A | * | 3/1971 | Schiff |
| 3,587,982 A | * | 6/1971 | Campbell |
| 3,767,085 A | * | 10/1973 | Cannon et al. |
| 4,107,793 A | * | 8/1978 | Wallace |
| 4,432,469 A | * | 2/1984 | Eble et al. |
| 4,471,888 A | * | 9/1984 | Herb et al. |
| 4,767,025 A | * | 8/1988 | Gebauer et al. |
| 4,934,827 A | * | 6/1990 | Taschke et al. |
| 4,951,843 A | * | 8/1990 | Paetow |
| 5,249,862 A | | 10/1993 | Herold et al. |
| 6,244,740 B1 | * | 6/2001 | Wagner et al. |
| 6,311,871 B1 | * | 11/2001 | Binder |

FOREIGN PATENT DOCUMENTS

| | | | |
|---|---|---|---|
| DE | 4235736 | * | 3/1994 |
| DE | 29705741 | * | 8/1998 |
| EP | 87029 | * | 8/1983 |
| EP | 0492412 | | 1/1992 |
| EP | 1110599 | * | 6/2001 |
| EP | 1149627 | * | 10/2001 |
| WO | 00/21652 | * | 4/2000 |
| WO | 01/24919 | * | 4/2001 |

\* cited by examiner

*Primary Examiner*—Charles E. Cooley
(74) *Attorney, Agent, or Firm*—Foley & Lardner

(57) ABSTRACT

The dynamic mixer comprises a rotor housing including a cover and a rotatable mixing rotor, the rotor housing cover being provided with inlets for the components to be mixed. For a good premixing of the components, the mixing rotor is provided near the inlets with a rotor disk whose surface is provided on the inlet side with carriers forming chamber sections for carrying along the components to be mixed, and whose circumference is provided with annular gaps through which the components pass to the rear side of the rotor disk and to the rotor hub which comprises mixing elements. Due to the fact that the components are carried along and transferred to the rear side of the rotor disk only at the circumference thereof, the components are metered and premixed, thereby allowing a substantial improvement of the mixing quality and performance.

18 Claims, 6 Drawing Sheets

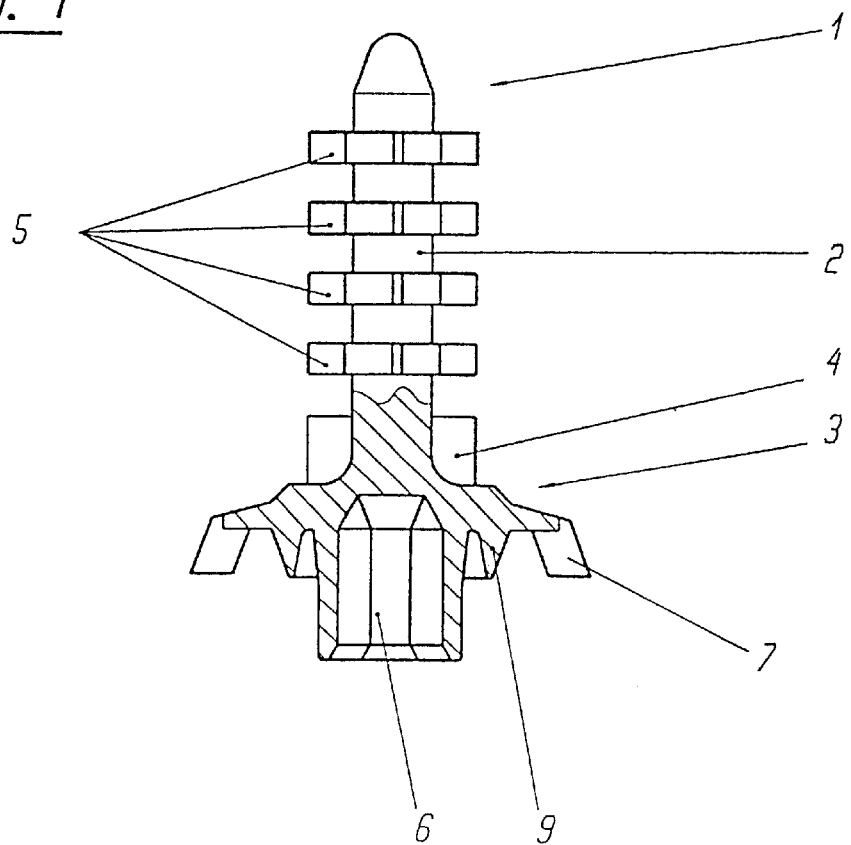
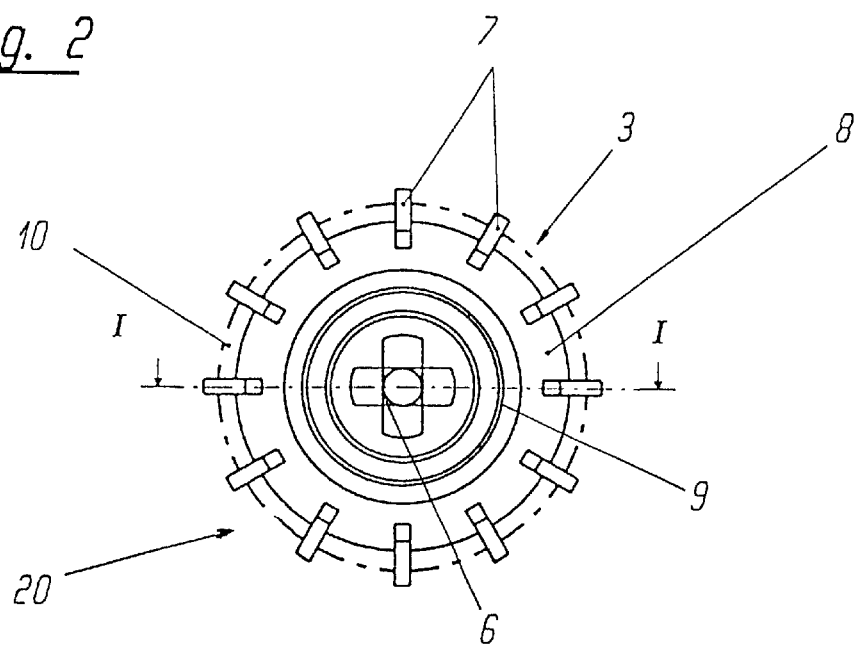

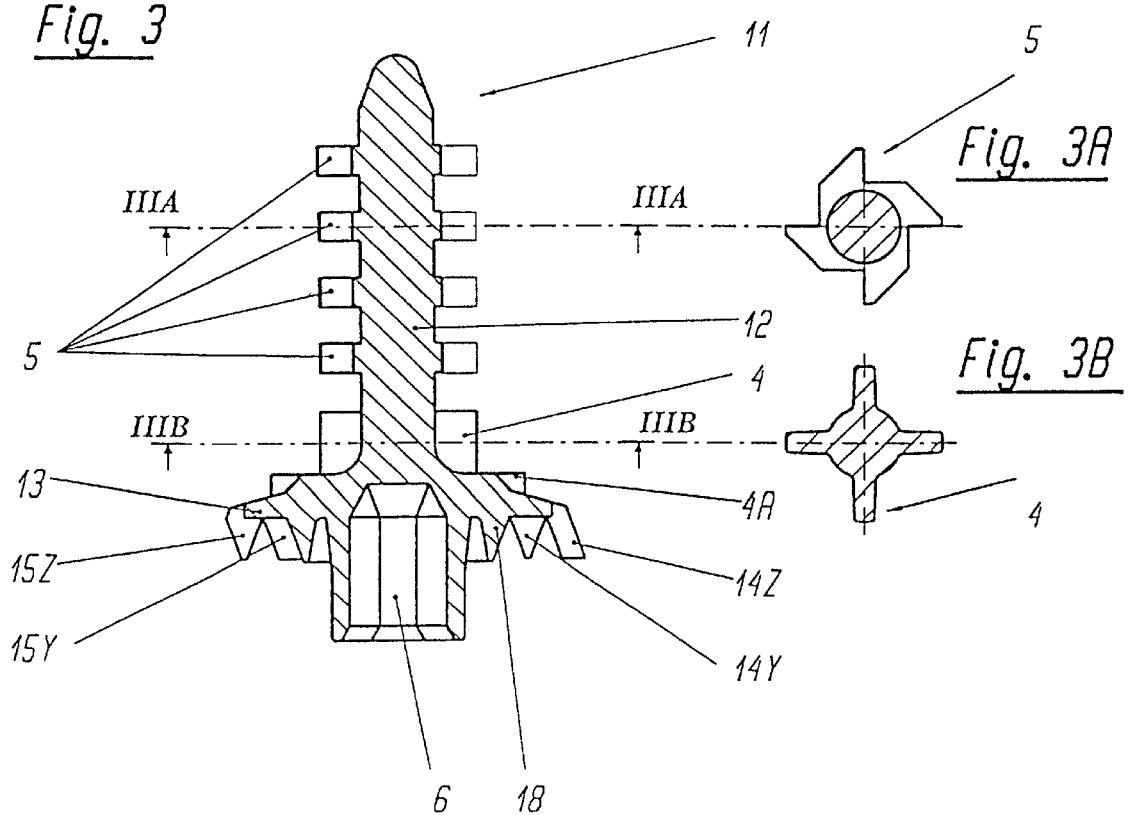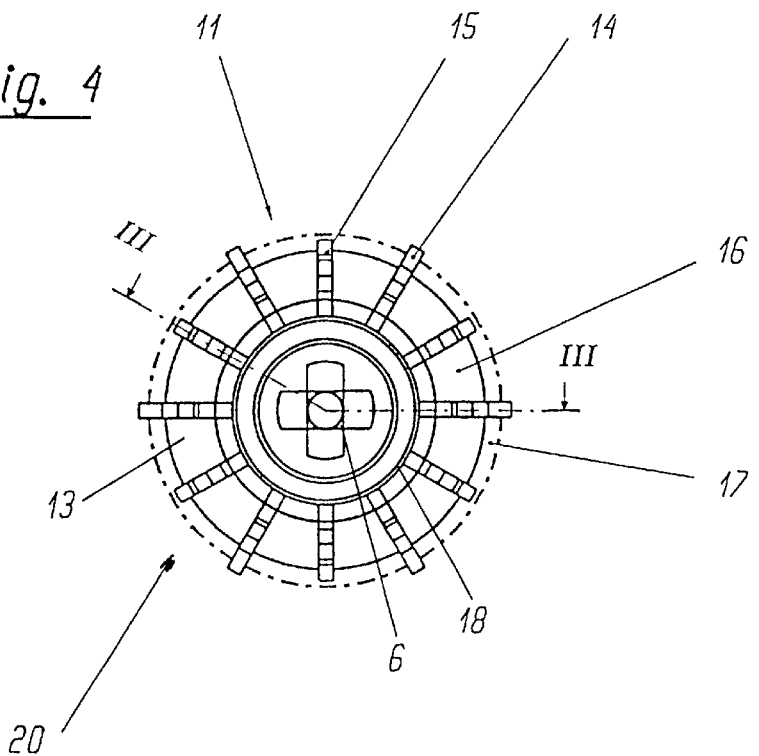

DYNAMIC MIXER

This Application claims benefit under 35 U.S.C. § 119(e) of Switzerland Application Number 1999 2210/99, filed Dec. 2, 1999 and Europe Application Number 00810432.5, filed May 18, 2000, the respective disclosures of which are incorporated by reference herein.

FIELD OF THE INVENTION

The present invention refers to a dynamic mixer comprising a rotor housing in which a rotatable mixing rotor is arranged, said rotor housing being closed by a plate-shaped cover on the inlet side which is provided with inlets for the components to be mixed.

BACKGROUND OF THE INVENTION

A mixer of this kind is known from European Patent Application No. 0,492,412. An essential feature of this mixer is a plate-shaped connecting member comprising a wiper of a particular design on the mixing rotor.

SUMMARY OF THE INVENTION

On the background of this prior art, it is the object of the present invention to provide a dynamic mixer allowing to achieve an improved mixing quality as well as an increased mixing performance. This object is attained by a dynamic mixer wherein the mixing rotor comprises a rotor disk for the purpose of premixing said components, which is disposed near the inlets and whose surface is provided on the inlet side with means for carrying along the components to be mixed, said rotor disk comprising gaps allowing the passage of said components to the back side of said rotor disk and to the rotor hub, which are provided with mixing elements.

Preferred embodiments of the invention are defined in the dependent claims.

BRIEF DESCRIPTION OF THE DRAWINGS

The invention will be explained in more detail hereinafter with reference to drawings of exemplary embodiments, where FIG. 1 shows a side elevation and partial section of a first embodiment of a mixing rotor of the invention;

FIG. 2 shows the mixing rotor of FIG. 1 as seen from the inlet side;

FIG. 3 shows a cross-section of a second embodiment of a mixing rotor of the invention according to line III—III in FIG. 4;

FIG. 3A shows a cross-section according to line IIIA—IIIA in FIG. 3;

FIG. 3B shows a cross-section according to line IIIB—IIIB in FIG. 3;

FIG. 4 shows the mixing rotor of FIG. 3 as seen from the inlet side;

DETAILED DESCRIPTION OF THE INVENTION

Figure 5:
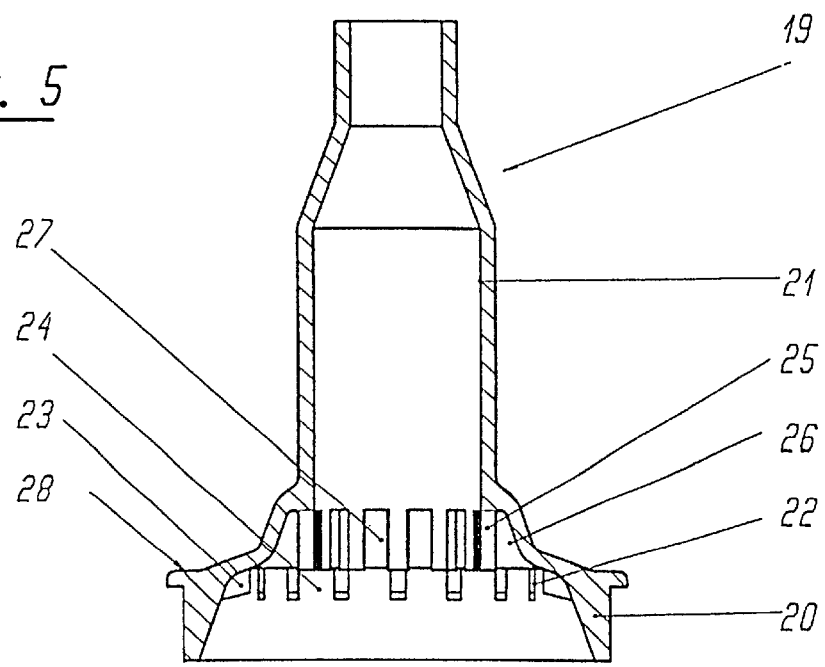
FIG. 5 shows the rotor housing of a mixer of the invention according to cross-section V—V in FIG. 6.
Figure 6:
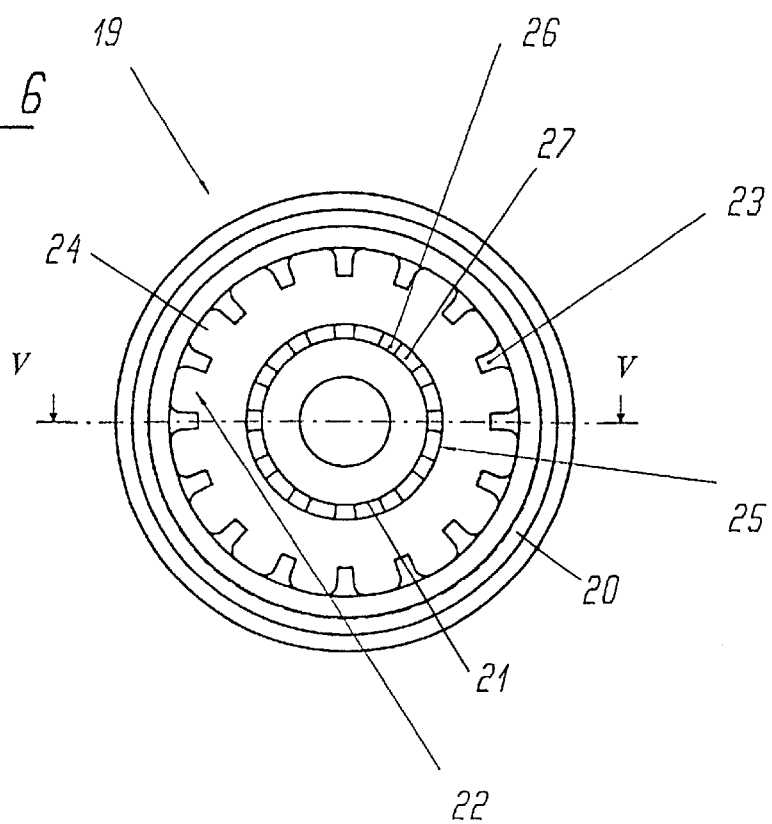
FIG. 6 shows the rotor housing of FIG. 5 as seen from the inlet side.

The dynamic mixer of the invention is composed of a mixing rotor and a rotor housing comprising a rotor housing cover. FIGS. 1 and 2 illustrate a first embodiment of a mixing rotor, and FIGS. 3 and 4 show a second one.

Mixing rotor 1 of FIGS. 1 and 2 essentially consists of a rotor hub 2 comprising a rotor disk 3 on the inlet side. The back side of the rotor disk is provided with mixing blades 4 which are followed by mixing projections 5. According to FIGS. 2 and 4, on the inlet side, the rotor hub comprises a driver opening 6 for engagement with the driver of the mixer driving shaft which may have various shapes, e.g. rectangular, hexagonal, or cross-recessed.

On the inlet side, the rotor disk is provided with chamber partitions 7 which divide the rotor disk into chamber sections 8. These sections serve for the metered, alternating and diametrically offset intake of the two components to be mixed and for their further transport. In order to prevent a stemming of the components, partitions 7 are shortened, i.e. they are not thoroughgoing. The rotor disk further comprises a collar 9 intended to cooperate with a sealing lip 34 attached to the rotor housing. Between the rotor housing and the circumference of the rotor disk, annular gaps 10 are created which are interrupted by partitions 7 and through which the components pass to the back side of the rotor disk and from there to the mixing elements in the cylindrical portion of the housing.

With reference to the second embodiment of a mixing rotor according to FIGS. 3 and 4, mixing rotor 11 with rotor hub 12 is provided with a rotor disk 13 on the inlet side. Mixing blades 4 as well as additional mixing blades 4A are disposed on the back side of the rotor disk and followed by mixing projections 5. FIG. 3A shows the cross-section of mixing projections 5 and FIG. 3B that of mixing blades 4.

On the inlet side, rotor disk 13 is provided with carriers of alternating outward extension, i.e. carriers 15 project less to the periphery than carriers 14. Carriers 14 and 15 have a tooth-shaped profile, and respective blades 15Y or 15Z provided on carrier 15 are staggered with respect to blades 14Y or 14Z on carrier 14.

In this manner, the inlet side of the rotor disk is divided into partly open chamber sections 16 which serve for the metered, diametrically offset and alternating intake and for the further transport of the two components to be mixed, thus contributing to premixing. In this embodiment as well, the components coming from the inlets can only pass to the back side of the rotor disk through the annular gaps between the circumference of the rotor disk and the rotor housing. However, it is also possible to provide annular gaps which are closer to the center, either combined with the peripheral gaps or exclusively. Furthermore, the rotor disk comprises a collar 18 intended to cooperate with the above-mentioned sealing lip.

Mixing rotor 1 or 11 is disposed in a bipartite rotor housing as illustrated in FIGS. 5 to 8. Rotor housing 19 according to FIGS. 5 and 6 comprises a plate-shaped housing portion 20 receiving rotor disk 13 and a cylindrical housing portion 21 receiving rotor hub 12. The bottom surface of plate-shaped housing portion 20 comprises a first, outer stator comb composed of individual ridges 23, the premixed components passing through the spaces 24 between the ridges to the second, inner stator comb 25 comprising inner ridges 26 with spaces 27 through which the premixed components pass to mixing blades 4A, 4 and to mixing projections 5 in order to be divided and mixed once again. The plate-shaped housing portion further comprises a contact surface 28 for a bayonet ring 35.

Figure 7:
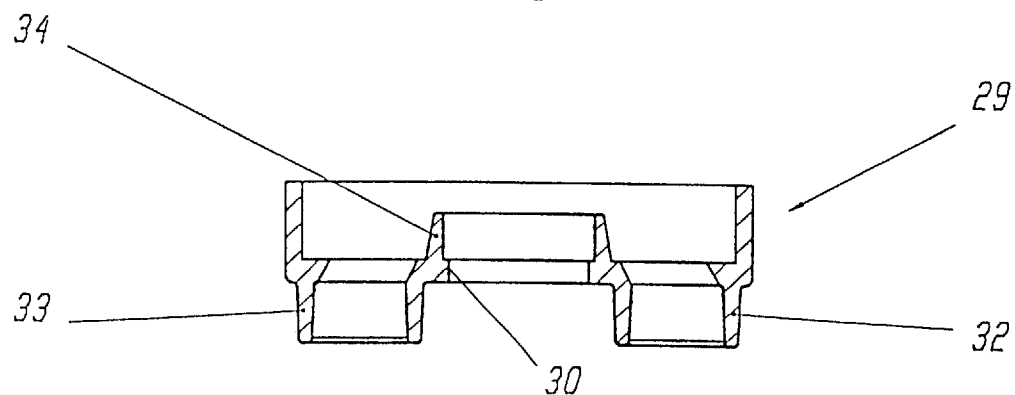
FIG. 7 shows the cover of the rotor housing of FIGS. 5 and 6 according to section VII—VII in FIG. 8.
Figure 8:
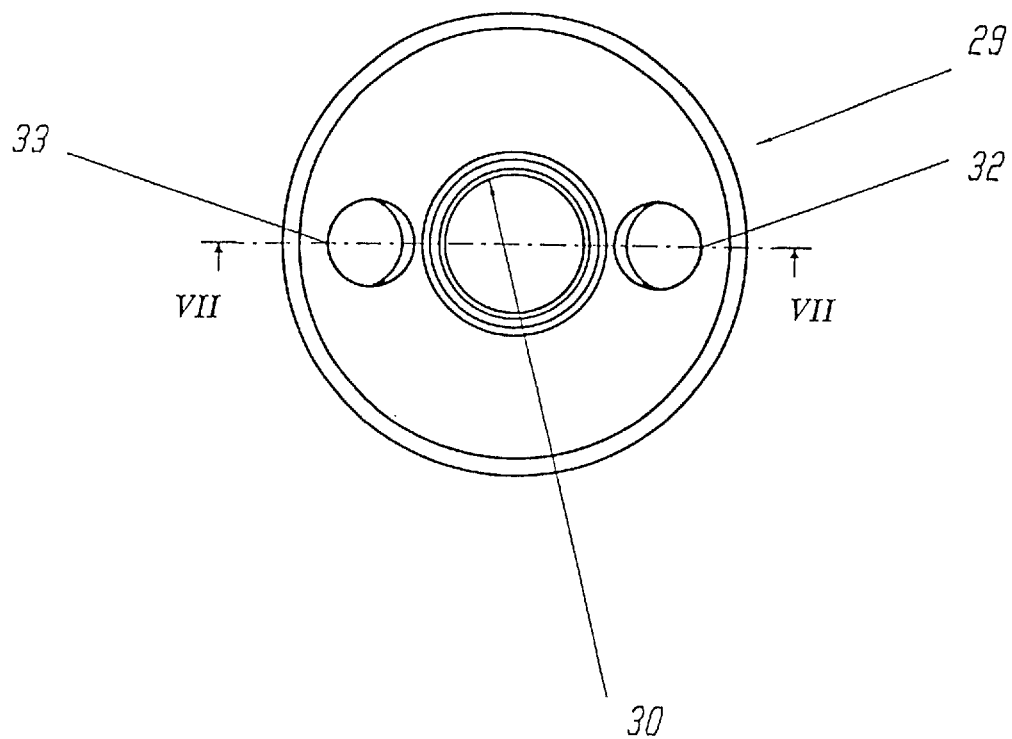
FIG. 8 shows the rotor housing cover as seen from the outlet side.

FIGS. 7 and 8 show a rotor housing cover 29 comprising a rotor bearing 30 receiving the carrier hub 31 and two similar inlets 32 and 33. For a good sealing of the carrier hub, rotor housing cover 29 is provided with a sealing lip 34.

It is also possible to provide further stator elements on cylindrical housing portion 21 in the area of the crowns of mixing projections in order to obtain a further improved mixing quality.

Figure 9:
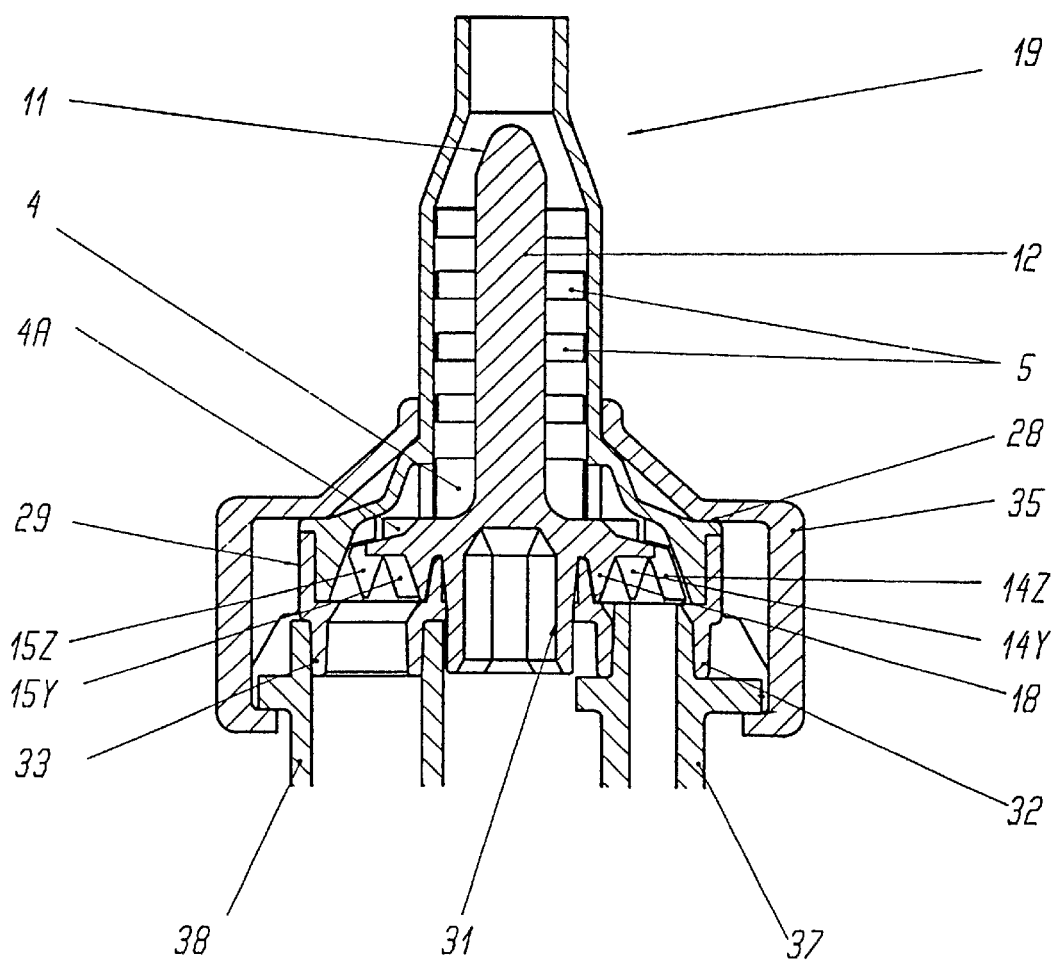
FIG. 9 shows a longitudinal section of the assembled mixer of FIGS. 3 to 8 connected to outlets of different diameters.
Figure 10:
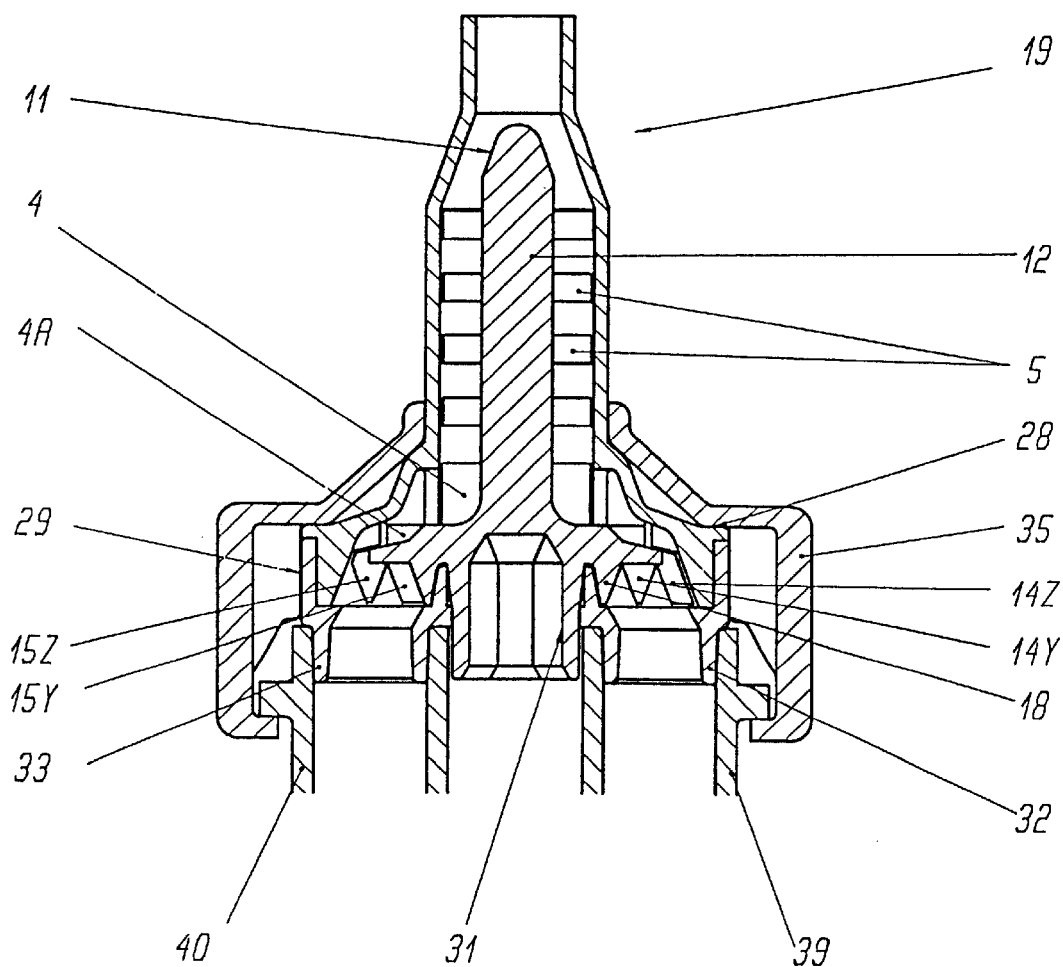
FIG. 10 shows a longitudinal section of the assembled mixer of FIGS. 3 to 8 connected to outlets of equal diameters.

FIGS. 9 and 10 illustrate that a suitably dimensioned mixer of the invention can be used both for double cartridges or dispensing appliances having outlets of equal diameters and for double cartridges or dispensing appliances having outlets of different diameters, even regardless of its orientation.

FIG. 9 shows a cross-section of an assembled mixer having equally dimensioned inlets, the mixer being connectable to a double cartridge or a dispensing appliance having containers of a cross-sectional ratio of 5:1 and outlets of different diameters. In FIG. 9, only outlets 37 and 38 are illustrated. One inlet 32 of the mixer fits over smaller outlet 37, and the other inlet 33 of the mixer fits into larger outlet 38, the mixer being attachable without a previous orientation.

FIG. 10 illustrates that the same mixer as in FIG. 9 is also connectable to a double cartridge or a dispensing appliance having equal outlets, the two inlets 32, 33 of the mixer being insertable into outlets 39, 40, again requiring no previous orientation.

In both embodiments, the mixer is secured by means of a bayonet ring 35 or alternatively an internally threaded screw nut. The same mixer can also be used for double cartridges or dispensing appliances having cross-sectional and outlet diameter ratios other than 1:1 and 5:1, e.g. 10:1.

As compared to known dynamic mixers of the same construction length, the described arrangement allows a substantially increased mixing power and quality at lower speeds and operates with a relatively low back pressure. The invention is not limited to the illustrated shapes but different shapes of the chamber sections and of the stator combs, mixing ridges, or mixing projections are possible within the scope of the invention.

What is claimed:

1. A dynamic mixer, comprising a rotor housing in which a rotatable mixing rotor is arranged, said rotor housing being closed by a plate-shaped cover on the inlet side which is provided with inlets for the components to be mixed, wherein said mixing rotor comprises a rotor disk for the purpose of premixing said components, which is disposed near the inlets and whose surface is provided on the inlet side with means for carrying along the components to be mixed, said rotor disk comprising gaps allowing the passage of said components to the back side of said rotor disk and to a rotor hub which are provided with mixing elements.

2. The dynamic mixer of claim 1, wherein said gaps have an annular shape and are provided at the circumference of said rotor disk.

3. The dynamic mixer of claim 1, wherein said means for carrying along said components are chamber partitions or carriers forming chamber sections.

4. The dynamic mixer of claim 3, wherein said carriers are of alternating outwardly extending longer and shorter carriers while the profiles of said longer carriers and said shorter carriers are provided with blades, said shorter carrier blades being staggered with respect to said longer carrier blades.

5. The dynamic mixer of claim 1, wherein the rotor housing is designed as a stator and is composed of a plate-shaped housing portion and of a cylindrical housing portion and wherein the bottom surface inside said plate-shaped housing portion comprises at least one stator comb through the spaces of which the components flow to said mixing elements.

6. The dynamic mixer of claim 5, wherein said plate-shaped housing portion comprises two concentrically disposed stator combs.

7. The dynamic mixer of claim 5, wherein additional stator elements are provided on the inside of said cylindrical housing portion in order to improve the mixing of the components.

8. The dynamic mixer of claim 1, wherein said mixing elements include mixing blades and mixing projections arranged in a crown.

9. The dynamic mixer of claim 1, wherein a sealing lip sealing a carrier hub is disposed on the inside of said rotor housing cover.

10. The dynamic mixer of claim 1, wherein said mixer is attachable to the outlet end of a double cartridge or of a dispensing appliance by means of a bayonet ring.

11. A dynamic mixer, comprising:

a rotor housing;

a rotatable mixing rotor arranged in said rotor housing, said rotor comprising a rotor disk on an inlet side and a rotor hub on an outlet side;

annular gaps formed between the rotor housing and a surface on the inlet side of the rotor disk, the annular gaps being interrupted by partitions which allow passage of components to be mixed; and mixing elements provided with at least one of said rotor hub and said rotor disk.

12. The dynamic mixer of claim 11, further comprising a plate-shaped cover attached to said rotor housing, said cover being provided with inlets for allowing entry of components to be mixed.

13. The dynamic mixer of claim 11, wherein the mixing elements comprise mixing blades provided on the rotor disk.

14. The dynamic mixer of claim 11, wherein the mixing elements comprise mixing projections provided on the rotor hub.

15. The dynamic mixer of claim 11, wherein the rotor disk includes chamber sections for carrying along the components to be mixed.

16. The dynamic mixer of claim 11, wherein said mixer is adapted to connect to a double cartridge or dispensing appliance having outlets of equal size.

17. The dynamic mixer of claim 11, wherein said mixer is adapted to connect to a double cartridge or dispensing appliance having different sized outlets.

18. The dynamic mixer of claim 11, wherein said mixer is adapted to attach to the outlet end of a double cartridge or to a dispensing appliance with a bayonet ring.

* * * * *